US00PP24208P2

(12) United States Plant Patent
Kordes

(10) Patent No.: US PP24,208 P2
(45) Date of Patent: Feb. 4, 2014

(54) MINIATURE ROSE PLANT NAMED 'KORPOT024'

(50) Latin Name: *Rosa hybrida*
Varietal Denomination: KORpot024

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 86 days.

(21) Appl. No.: 13/385,825

(22) Filed: Mar. 7, 2012

(51) Int. Cl.
*A01H 5/00* (2006.01)

(52) U.S. Cl.
USPC ..... Plt./121; Plt./101; Plt./116

(58) Field of Classification Search
USPC ..... Plt./101, 116, 121
See application file for complete search history.

*Primary Examiner* — Susan McCormick Ewoldt

(57) ABSTRACT

A new and distinct variety of rose with long lasting, novel hot pink flowers, and attractive foliage with above average disease resistance. It exhibits vigorous growth with abundant flowers. The new variety propagates well from cuttings. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The present discovery constitutes a new and distinct variety of a miniature pot rose plant which was discovered in a cultivated area in the nursery of the inventor in Offenseth-Sparrieshoop, Germany in June, 2010. The new rose variety resulted from a naturally occurring mutation of unknown causation on a branch of 'KORpolare', a patented rose described and illustrated in U.S. Plant Pat. No. 18,840, and issued on May 27, 2008.

The new rose plant was asexually propagated for further evaluation. This new and distinctive miniature rose variety is named 'KORpot024'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from 'KORpolare', by the following combination of characteristics:

1. 'KORpot024' has hot pink flowers, whereas 'KORpolare' has dark red flowers.
2. 'KORpot024' flowers have approximately 30 pistils, whereas 'KORpolare' flowers have approximately 85-95 pistils.

The new and distinct rose plant was selected due to its:

1. Uniform growth and flowering;
2. Abundant attractive, recurrent hot pink flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpot024' from all other varieties of which I am aware.

As part of the rose development program, Tim-Hermann Kordes asexually propagated the mutation by rooting cuttings and conducted evaluations and observations on the resulting plants in a controlled environment in Offenseth-Sparrieshoop, Germany. The resulting seedlings exhibited distinctive physical and biological characteristics. The first asexual reproduction of 'KORpot024' was done by rooting softwood cuttings in June, 2010 at the Rosa-Danica Nursery in Odense, Denmark.

This initial and other subsequent propagations conducted in controlled environments demonstrate that 'KORpot024' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot024'.

DETAILED BOTANICAL DESCRIPTION

The following is a description of 'KORpot024', as observed growing in October, 2011 in a nursery in Jackson County, Oreg. on plants of 4 months of age. Color references are made using The Royal Horticultural Society (London, England) Colour Chart, 2001 except where common terms of color are used.

For a comparison, several physical characteristics of the rose variety 'KORcarill', a rose variety from the same inventor described and illustrated in U.S. Plant Pat. No. 15,716 and issued on Apr. 12, 2005 are compared to 'KORpot024' in Chart 1.

CHART 1

| Characteristic | 'KORpot024' | 'KORcarill' |
|---|---|---|
| Petal number | 50-60 petals | 34-38 petals |
| Sepal length | 30-40 mm | 25 mm |
| Pistil number | Approximately 30 | Approximately 50-60 |

Parents: 'KORpolare'.
Classification:
*Botanical classification.*—*Rosa hybrida* 'KORpot024'.
*Commercial classification.*—Miniature rose.

FLOWER AND FLOWER BUD

Blooming habit: Continuous.
Flower bud:
*Size.*—Upon opening, 25 mm in length from base of receptacle to distal end of bud and 18-20 mm in diameter at its widest point.
*Bud form.*—Long, ovate, with a flat base.
*Bud color.*—As sepals first unfold, bud color is Red-Purple Group N57B. When ¼ open, the upper surface of petals is Red-Purple Group N57C, and the lower surface is Red-Purple Group N57B. Guard Petals are Red-Purple Group N57C with a thin stripe in the center of White Group 155D.
Sepals:
*Color.*—Upper surface: Green Group 137B. Lower surface: Green Group 138B.
*Size.*—Average 30-40 mm (l)×5 mm (w).
*Shape.*—Strong foliaceous appendages on 3 of the 5 sepals. Apex: Irregular shape, pointed. Base: Flat at union with receptacle.
*Quantity.*—Five.
*Surface texture.*—Upper side: Slightly pubescent. Lower surface: Pubescent with no stipitate glands.
*Margins.*—Entire.
Receptacle:
*Surface.*—Smooth to lightly pubescent.
*Color.*—Yellow-Green Group 144A.
*Shape.*—Urn-shaped.
*Size.*—8 mm (h)×7 mm (w).
Peduncle:
*Surface.*—With fine hairs and stipitate glands.
*Length.*—45 to 50 mm average length.
*Diameter.*—2 to 4 mm average diameter.
*Color.*—Yellow-Green Group 146C.
*Strength.*—Strong.
*Borne.*—Singularly.
Flower bloom:
*Fragrance.*—None.
*Duration.*—On the plant approximately 15 to 16 days. Long lasting. As a cut flower, 6 to 8 days. Senesced petals drop away cleanly.
*Size.*—Above average for a miniature rose. When open, the average flower diameter is 50 mm and the average flower height is 15-20 mm.
*Form.*—Shape of flower when viewed from the side: Upon opening, upper part: Flat. Upon opening, lower part: Convex. Open flower, upper part: Flattened convex. Open flower, lower part: Flattened convex.
Color:
*Upon opening, petals.*—Outermost petals: Outer Side: Red-Purple Group 67C. Inner Side: Red-Purple Group N66B. Innermost petals: Outer Side: Red-Purple Group N66B. Inner Side: Red-Purple Group N66B.
*Upon opening, basal petal spots.*—Basal petal spot, outermost petals: Outer Side: Green-White Group 157B. Inner Side: Green-White Group 157B. Basal petal spot, innermost petals: Outer Side: White Group 155C. Inner Side: White Group 155C.
*After opening, petals.*—Outermost petals: Outer Side: Red-Purple Group 63B. Inner Side: Red-Purple Group 67A. Innermost petals: Outer Side: Red-Purple Group 67B. Inner Side: Red-Purple Group 64C. Outer and inner petals have an occasional stripe of White Group N 155C, found on both sides of the petal. This intonation is variable, affecting 50% of petals in some flowers and only a few petals in others, and becomes more pronounced as blooms open.
*After opening, basal petal spots.*—Basal petal spot, outermost petals: Outer Side: White Group 155D. Inner Side: White Group 155B. Basal petal spot, innermost petals: Outer Side: White Group 155C. Inner Side White Group 155D.
General tonality: On open flower Red-Purple Group 61C. No change in the general tonality at the end of the 7$^{th}$ day. Afterwards, general tonality is Red-Purple Group 64C.
Petals:
*Petal count.*—Very double.
*Average range.*—Approximately 50-60 petals under normal conditions.
*Petal reflex.*—Petals reflex strongly.
*Petal edge.*—Undulated.
*Petal shape.*—Ovoid. Apex shape is round. Shape of base is deltoid.
*Petal size.*—22 mm (l)×15 mm (w).
*Thickness.*—Thin.
*Petal arrangement.*—Not formal.
Petaloids:
*Petaloid count.*—Average of 8 to 12 per flower.
*Petaloid size.*—Petaloids are 12 mm (l)×18 mm (w).
*Petaloid color.*—Color of inner side is Red-Purple Group 66B. Color of outer side is Red-Purple Group 61C.
*Petaloid texture.*—Smooth.
*Margins.*—Undulated.
*Petaloid shape.*—Most commonly deltoid, with some petaloids highly irregular. Apex: Round. Base: Deltoid.
Reproductive organs:
*Pistils.*—Average, approximately 30 present. Stigmas: Location: Slightly superior in position to anthers. Color: White Group 155A. Styles: Length: About 5 mm long. Color: Green-Yellow Group 1D with intonations of Red-Purple Group 63C on the upper side.
*Stamens.*—Approximately 70 on average and regularly arranged. Anthers: Size: Average 8 mm long. Pollen: Generally present. Color: Yellow-Orange Group 20A. Filaments: Color: Green-Yellow Group 1C. Length: 4 mm.

THE PLANT

*Growth.*—Vigorous growth.
*Plant habit.*—Compact, upright habit. When grown as a 15 cm pot plant, the average plant height is 25-30 cm and the average plant width is 25 cm.
*Stems.*—Stem color: Young wood: Yellow-Green Group 146A. Older wood: Yellow-Green Group 144A. Stem surface: Young wood: Smooth. Older wood: Smooth.
*Prickles.*—Present. Incidence: Average of 3 per each 10 cm of stem. Size: Average length: 4 mm. Color: Immature prickles: Green-White Group 157A.

Mature prickles: Greyed-Orange Group 164D. Shape: Linear. Anthocyanin: Greyed-Red Group 182B.

Leaves and leaflets: Normally 5-7 leaflets on normal leaves in middle of the stem.

*Venation pattern.*—Pyramidal net pattern.

*Leaf size.*—70 mm (l)×45 mm (w).

*Abundance.*—Average.

*Texture.*—Smooth. Upper side of leaflet: Semi-glossy. Under side of leaflet: Matte.

*Color, mature foliage.*—Upper Leaf Surface: Green Group 139A. Lower Leaf Surface: Green Group 138B.

*Color, juvenile foliage.*—Upper Leaf Surface: Green Group 139B. Lower Leaf Surface: Green Group 138B.

*Anthocyanin intonation.*—Greyed-Red Group 181C present on edges of juvenile foliage, petiole, and rachis.

*Stipules.*—Size: 12 mm long. Stipule color: Yellow-Green Group 146B. Margins: With stipitate glands. Shape: Apex: Apiculate. Base: Deltoid.

*Petiole.*—Length: Average 20 mm. Diameter: Average 3 mm. Petiole color: Green Group 137B. Underneath: Green Group 137C with center of Yellow-Green Group 147D. Margins: Uneven with pubescence and occasional stipitate glands. Anthocyanin: Greyed Red Group 181C. Prickles: None observed. Stipitate Glands: Limited numbers on underside of petiole.

*Petiole rachis.*—Length: Average 9 mm. Diameter: Average 2 mm. Color: Green Group 137B-137C. Anthocyanin present on juvenile tissue. Greyed-Purple Group 183D along margins. Margins: Rough with limited numbers of stipitate glands. Prickles: A few small prickles underneath.

*Leaflets.*—Size: Average size of the terminal leaflet is 25 mm (l)×15 mm (w). Shape: Ovate. Base: Obtuse. Apex: Acute. Margins: Finely serrated. Surface: Upper: semi-glossy. Lower: Matte. Texture: Thick. Arrangement: Odd pinnate. Venation Reticulate.

Hips/seed formation: None observed.

Winter hardiness: Unknown.

Disease resistance: Above average resistance to Powdery mildew (*Sphaerotheca pannosa*) and *Botrytis* (*Botrytis cinerea*) diseases under normal growing conditions.

I claim:

1. A new and distinct variety of rose plant, as described and illustrated herein.

* * * * *

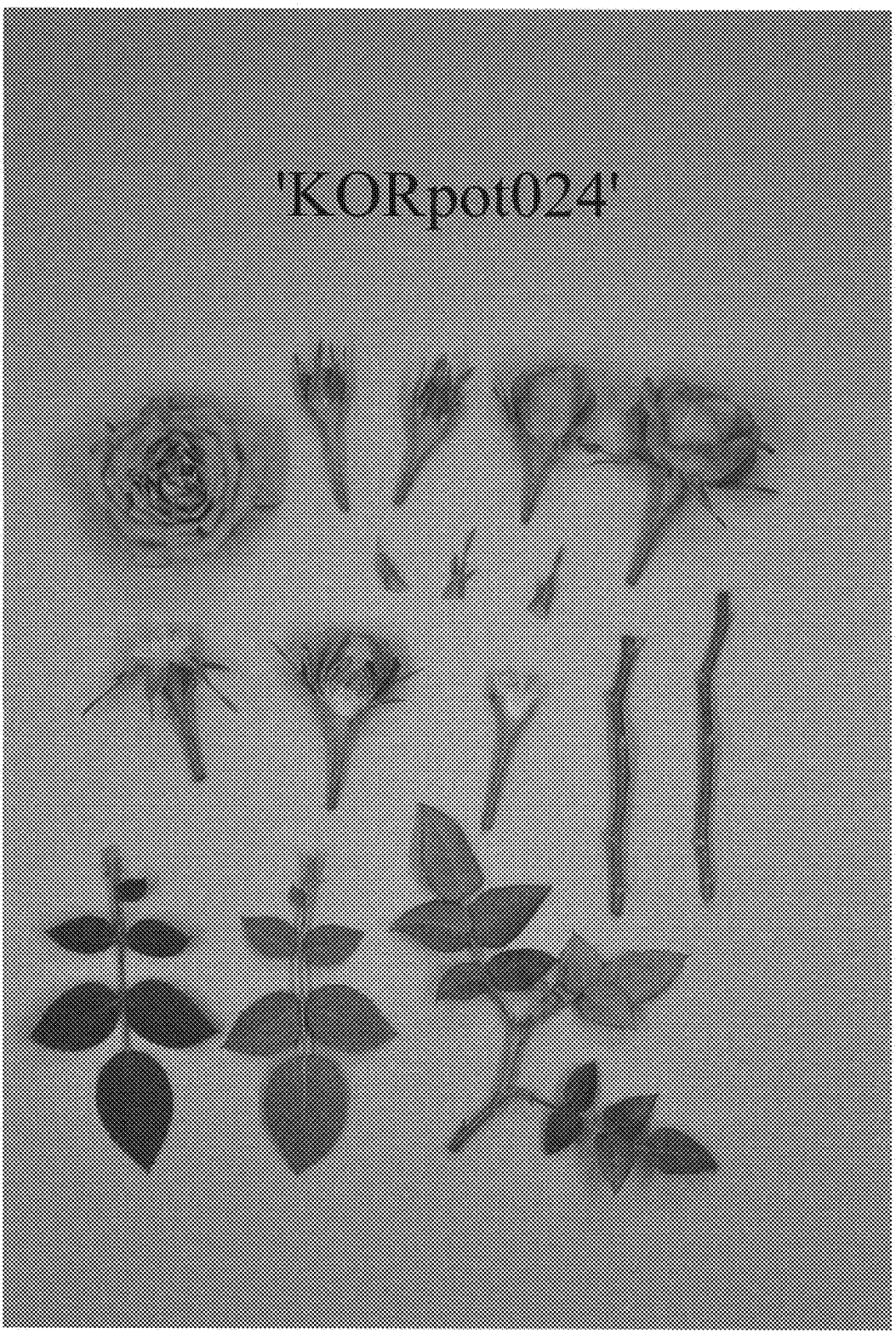
'KORpot024'